(12) United States Patent
Zhou et al.

(10) Patent No.: US 8,048,377 B1
(45) Date of Patent: Nov. 1, 2011

(54) IMMOBILIZING CHEMICAL OR BIOLOGICAL SENSING MOLECULES ON SEMI-CONDUCTING NANOWIRES

(75) Inventors: Zhang-Lin Zhou, Mountain View, CA (US); Zhiyong Li, Mountain View, CA (US); Sean Xiao-An Zhang, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 2205 days.

(21) Appl. No.: 10/795,730

(22) Filed: Mar. 8, 2004

(51) Int. Cl.
*G01N 27/00* (2006.01)
*C12M 1/00* (2006.01)
*G01N 21/75* (2006.01)

(52) U.S. Cl. ............... 422/82.02; 422/400; 422/401; 422/82.01; 977/700; 977/742; 977/745; 977/842; 204/403.01

(58) Field of Classification Search .......... 422/50, 422/68.1, 82.01, 82.02, 83, 98; 977/700, 977/762, 953, 958; 436/43
See application file for complete search history.

(56) References Cited

U.S. PATENT DOCUMENTS

| | | | |
|---|---|---|---|
| 4,334,880 A | 6/1982 | Malmros | |
| 4,444,892 A | 4/1984 | Malmros | |
| 5,766,934 A | 6/1998 | Guiseppi-Elie | |
| 6,286,226 B1 * | 9/2001 | Jin | 33/706 |
| 6,785,432 B2 * | 8/2004 | Letant et al. | 385/12 |
| 6,815,706 B2 * | 11/2004 | Li et al. | 257/14 |
| 6,869,671 B1 * | 3/2005 | Crouse et al. | 428/304.4 |
| 7,052,588 B2 * | 5/2006 | Gu et al. | 204/403.01 |
| 7,129,554 B2 * | 10/2006 | Lieber et al. | 257/414 |
| 2003/0134433 A1 | 7/2003 | Gabriel et al. | |
| 2003/0175161 A1 | 9/2003 | Gabriel et al. | |
| 2003/0218224 A1 | 11/2003 | Schlaf et al. | |

FOREIGN PATENT DOCUMENTS

| | | |
|---|---|---|
| JP | 2002542794 A | 12/2002 |
| JP | 2003504595 A | 2/2003 |
| JP | 2003517604 A | 5/2003 |
| WO | WO-0065099 | 11/2000 |
| WO | WO-0102538 A1 | 1/2001 |
| WO | WO 01/44796 A1 | 6/2001 |
| WO | WO-0248701 | 6/2002 |

OTHER PUBLICATIONS

High accuracy electrometers for low current/high resistance applications, Keithley, 2002, pp. 1-12.*

Cui, Yi, Qingqiao Wei, Hongkun Park and Charles M. Lieber, "Nanowire ananosensors for Highly Sensitive and Selective Detection of Biological and Chemical Species," Science, vol. 293, Aug. 17, 2001, pp. 1289-1292.

Foulds, Nicola C. and Christopher R. Lowe, "Enzyme Entrapment in Electrically Conducting Polymers," I. Chem. Soc., Faraday Trans. 1, 1986, 82, 1259-1264.

Gee, Kyle R., Zhang-Lin Zhou, Wei-Jun Qian and Robert Kennedy, "Detection and Imaging of Zinc Secretion from Pancreatic B-Cells Using a New Fluorescent Zinc Indicator," J. Am Chem. vol. 124, No. 5, 2002 776-778.

Gee, K.R., Z.-L. Zhou, D. Ton-That, S.L. Sensi and J.H. Weiss, "Measuring Zinc in Living Cells. A New Generation of Sensitive and Selective Fluorescent Probes," Cell Calcium (2002) 31(5), 245-251.

Iwakura, Chiaki, Yoshio Kajiya and Hiroshi Yoneyama; "Simultaneous Immobilization of Glucose Oxidase and a Mediator in Conducting Polymer Films," J. Chem. Soc., Chem Commun., 1988 pp. 1019-1020.

Umaña, Mirtha and Jess Waller, "Protein-Modified Electrodes. The Glucose Oxidase/Polypyrrole System," Anal. Chem. 1986, 58, 2979-2983.

Malmros, M.K., J. Gulbinski, III and William B. Gibbs, Jr., "A Semiconductive Polymer Film Sensor for Glucose," Biosensors 3 (1987/88) 71-87.

Yi Cui et al, "Nanowire nanosensors for Highly Sensitive and Selective Detection of Biological and Chemical Species", Science, V 293, Aug. 17, 2001.

Robert J Chen et al, "Noncovalent Functionalization of Carbon Nanotubes for Highly Specific Electronic Biosensors", www.pnas.org/cgi.

Andrei Kolmakov et al, "Detection of CO and O2 Using Tin Oxide Nanowire Sensors", Adv. Mater. 2003, 15, No. 12, Jun. 17.

Pengfei Qi et al, "Toward Large Arrays of Multiplex Functionalized Carbon Nanotube Sensors for Highly Sensitive and Selective Molecular Detection", Nano Letters, V.3(3), 2003.

Hewlett-Packard Development Co. L.P., List of References Cited, Office Action issued by Japanese Patent Office, App. No. JP2005-63445 Dated Feb. 9, 2010.

* cited by examiner

*Primary Examiner* — Jill Warden
*Assistant Examiner* — Neil N Turk

(57) ABSTRACT

The present invention is drawn toward a chemical or biological sensor that can comprise a semi-conducting nanowire and a chemical or biological sensing molecule tethered to the semi-conducting nanowire through a spacer group including a hydrophilic reactive group. In one embodiment, the semi-conducting nanowire can be part of an array of like or similar semi-conducting nanowires. Electrical leads can provide an electrical current to the array, and a signal measurement apparatus can be electrically coupled to the array, and can be configured for detecting changes in the electrical current of the array.

56 Claims, No Drawings

US 8,048,377 B1

IMMOBILIZING CHEMICAL OR BIOLOGICAL SENSING MOLECULES ON SEMI-CONDUCTING NANOWIRES

FIELD OF THE INVENTION

The present invention relates generally to chemical and biological analysis. More particularly, the present invention relates to the preparation of functionalized nanowires for use as chemical or biological analysis.

BACKGROUND OF THE INVENTION

Chemical analysis and the identification of biological materials have been carried out in the areas of analytical biology, chemistry, and physics. Typically, analytical methods used in these disciplines have required the use of cumbersome laboratory instrumentation in a centralized laboratory and long sampling and analysis times. However, increasing awareness and concern regarding factors that influence health, safety, appliance performance, and the environment have created a demand for user-friendly technologies capable of detecting, identifying, and monitoring chemical, biological, and environmental conditions in real-time. Given these trends, it is safe to predict that intelligent, portable, wireless, web-enabled, self-diagnostic appliances exploiting a broad range of chemical and biosensor technology will be in demand in the near future.

A number of conventional methods have been developed for detection of chemical or biological agents. For example, the immobilization of indicator biomolecules onto conductive polymer substrates as well as the development of chemical and biological sensor devices based on electroconductive polymers is an area that has attracted considerable recent attention. However, these conventional chemical and/or biosensors are designed to operate in aqueous solution environments, not in the air or in the solid state.

In recent years, chemical or biological sensors based on semi-conducting nanowires, such as silicon and germanium, have become more important, as such nano-scale sensors can offer high sensitivity, low cost, high density arrays, and low power consumption, which characteristics are difficult to achieve with conventional sensors. As such, research in this area of chemical or biological sensing is ongoing.

SUMMARY OF THE INVENTION

It has been recognized that it would be advantageous to develop semi-conducting nanowire chemical or biological sensors that are functionalized to provide desired sensing capabilities. It has also been discovered that a convenient, reproducible, and robust immobilization of chemical/biological sensing molecules on the surface of semi-conducting nanowires will dramatically improve the quality and the reusability of such sensors. With this recognition in mind, a chemical or biological sensor can comprise a semi-conducting nanowire and a chemical or biological sensing molecule tethered to the semi-conducting nanowire through a spacer group including a hydrophilic reactive group.

In another embodiment, a chemical or biological sensor can comprise an array of semi-conducting nanowires, electrical leads that provide an electrical property to the array, and a signal measurement apparatus electrically coupled to the array and configured for detecting changes in the electrical property, which can be electrical current carried by the array. The array can include individual semi-conducting nanowires, each including chemical or biological sensing molecules tethered thereto through a spacer group including a hydrophilic reactive group.

In another embodiment, a method of detecting the presence of an analyte in an environment can comprise multiple steps. One such step includes applying an electrical current along a nanowire sensing element of a chemical or biological sensor, wherein the nanowire sensing element includes a semi-conducting nanowire and a chemical or biological sensing molecule tethered to the semi-conducting nanowire through a spacer group including a hydrophilic reactive group. Additional steps can include exposing the nanowire sensing element to an environment suspected of containing an analyte that is interactive with the chemical or biological sensing molecule, and determining whether the conductance is altered as a result of the analyte interacting with the chemical or biological sensing molecule.

Additional features and advantages of the invention will be apparent from the detailed description that follows, which illustrates, by way of example, features of the invention.

DETAILED DESCRIPTION OF THE PREFERRED EMBODIMENT(S)

Reference will now be made to the exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting.

It must be noted that, as used in this specification and the appended claims, the singular forms "a," "an," and "the" include plural referents unless the content clearly dictates otherwise.

The term "semi-conducting nanowire" includes elongated structures of semi-conducting material, such as silicon, germanium, gallium arsenide, tin oxide, cadmium sulfide, cadmium telluride, cadmium selenide, or the like, which have a narrow cross-section, e.g., less than 100 nm. The nanowires can have an aspect ratio (length to width) that is greater than about 5. In other words, nanowires are generally elongated by at least five times along an axis with respect to other perpendicular axes. The term "nanowire" does not imply that the structure must be wire-like, only that the structure is elongated along one of its axes. For example, structures that are wire-like, tubular, rope-like, or belt-like are considered to be nanowires. More specifically, traditional nanowires, nanotubes, nanoropes, and nanobelts are all considered to be nanowires in accordance with embodiments of the present invention. Additionally, a specific reference to a type of material does not imply that a single compositional component is necessarily present. For example, a "silicon nanowire" can include a traditional nanowire, nanotube, nanorope, or nanobelt that can be primarily or totally silicon, or can be a composite or hybrid nanowire, such as a boron-doped silicon nanowire, nanotube, nanorope, or nanobelt. Semi-conducting nanowires can be prepared by one of several methods, such as by growing methods or by fabrication methods wherein e-beam lithographic or nanoimprinting methods are used to form the nanowire. When growing nanowires on a substrate, the use of chemical vapor deposition on catalyst nanoparticles as a nucleation site can be used. Thus, well-controlled sizes, patterns, and/or densities of nanowires can be grown in an array. These nanowires can remain attached to the substrate and used as a chemical or biological sensor, or can be harvested for inclusion in a chemical or biological sensor. Other specific exemplary methods for forming nanowires include template assistance methods, electrochemical deposition methods, high pressure injection methods, chemical vapor deposition methods, and laser assisted methods, each of which is generally known in the art. Without being bound by particular dimensions, in certain embodiments, individual semi-conducting nanowires can be from about 10 nm to 100 nm in width.

"Analyte" shall mean a substance that may be present in a fluid, gas or solid state environment that is being tested for using the chemical or biological sensing molecule-modified semi-conducting nanowires of the present invention. Specifically, the analyte can be a chemical or of a chemical class, or can be a biological substance or of a biological class.

The term "electrical property" includes properties commonly known in the electrical arts, such as current, capacitance, voltage, resistance, etc.

The term "lower" when referring to alkyl groups, alkoxy groups, or the like, includes compositions having a $C_1$-$C_4$ carbon chain, e.g., methyl, methoxy, ethyl, ethoxy, propyl, isopropyl, butyl, isobutyl, etc.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 μm to about 200 μm should be interpreted to include not only the explicitly recited limits of 1 μm and about 200 μm, but also to include individual sizes such as 2 μm, 3 μm, 4 μm, and sub-ranges such as 10 μm to 50 μm, 20 μm to 100 μm, etc.

The term "about" when referring to a numerical value or range is intended to encompass the values resulting from experimental error that can occur when taking measurements.

In accordance with an embodiment of the present invention, a chemical or biological sensor can comprise a semi-conducting nanowire and a chemical or biological sensing molecule tethered to the semi-conducting nanowire through a spacer group including a hydrophilic reactive group.

In another embodiment, a chemical or biological sensor can comprise an array of semi-conducting nanowires, electrical leads that provide an electrical current to the array, and a signal measurement apparatus electrically coupled to the array and configured for detecting changes in the electrical current carried by the array. The array can include individual semi-conducting nanowires, each including chemical or biological sensing molecules tethered thereto through a spacer group including a hydrophilic reactive group.

In another embodiment, a method of detecting the presence of an analyte in an environment can comprise multiple steps. One such step includes applying a voltage or current along a nanowire sensing element of a chemical or biological sensor, wherein the nanowire sensing element includes a semi-conducting nanowire and a chemical or biological sensing molecule tethered to the semi-conducting nanowire through a spacer group including a hydrophilic reactive group. Additional steps can include exposing the nanowire sensing element to an environment suspected of containing an analyte that is interactive with the chemical or biological sensing molecule, and determining whether the current is altered as a result of the analyte interacting with the chemical or biological sensing molecule.

As described, chemical or biological sensing molecules can be attached to the surface of the semi-conducting nanowires to form a functionality that can be configured to sense the presence of an analyte. Specifically, in one embodiment, a current can be applied to a semi-conducting nanowire including an attached chemical or biological sensing molecule. The nanowire can also be electrically coupled to a sensing device that can detect minimal changes in current. In one example, changes on the order of Pico amperes can be detected. Thus, when the chemical or biological sensing molecule interacts or reacts with a predetermined analyte, the conductance of the nanowire can change, which can be detected by the sensing device. Because of the large ratio of surface area to the volume of the nanowires, interaction with small number of analyte compositions on the surface can be detectable. In this embodiment, the nanowires can be configured such that two locations of the nanowire are attached to electrical leads to apply the current. Alternatively, the nanowire can be a free-standing nanowire of an array of freestanding nanowires, which can also be used as a chemical or biological sensor.

The chemical or biological sensing molecules can be used for detecting chemical or biological substances/agents, such as metal ions, peptides, proteins, nucleic acids, enzymes, antibodies, and/or pathogens. These materials can be adapted for use in an aqueous or organic solution or dispersion, and can also be adapted for use in solid state or gaseous environments. For example, by immobilizing a fluorescent probe on a semi-conducting nanowire, gaseous or solid environment sensing can be realized.

In accordance with embodiments of the present invention, a practical chemical process is provided for immobilizing chemical or biological sensing molecules onto a semi-conducting nanowire. In a specific embodiment, by treating a silicon nanowire with certain chemical reagents, such as 3-aminopropyltriethoxysilane or tetrachlorosilane, one can introduce a reactive group onto the semi-conducting nanowire. The reactive group can be configured to be reactive with a chemical or biological sensing molecule to form a stable covalent bond between silicon surface and the molecular sensing molecule. When attaching a chemical or biological sensing molecule to a silicon surface, the reaction should be controlled such that at least one sensing moiety of the sensing molecule is free to interact with the environment. In other words, the attachment mechanism should not destroy a functionality of the sensing moiety of the molecule used to modify the semi-conducting nanowire surface. If configured properly, the chemical or biological sensing molecule can be firmly attached to the silicon surface via a covalent bond, allowing for detection of chemical reagents and/or biological species in an environment. The nano-scale chemical or biological sensors prepared can be well suited for use in liquid environments, gaseous environments, and in solid state applications.

Provided herein are several exemplary preparative schemes that can be used to prepare chemical or biological sensing semi-conducting nanowires in accordance with embodiments of the present invention. The chemical or biological sensing molecule can be attached to a semi-conducting nanowire in accordance with Formula 1 as follows:

NW-B-A-M          Formula 1

In Formula 1 above, NW is a semi-conducting nanowire (including traditional nanowires, nanotubes, nanoropes, and nanobelts), B is a bridging group, A is an spacer group, and M is a chemical or biological sensing molecule.

The chemical or biological sensing molecule (M) can include a potential sensing molecular unit, such as those used as ion indicators, pH indicators, DNA stains, protein stains, enzyme indicators, etc. In one embodiment, the sensing molecule can be a fluorescent dye, which can include, but is not limited to 4,4-difluoro-4-bora-3a,4a-diaza-s-indacene (BO-DIPY) dye, fluorescein and substituted fluorescein dye, rhodamine and substituted rhodamine dye, coumarin and substituted coumarin dye, naphthalene and substituted naphthalene dye, pyrene and substituted pyrene dye, pyridyloxazole dye, 7-nitrobenz-2-oxa-1,3-diazole derivative dyes, anthracene and substituted anthracene derivative dyes, eosin and erythrosine derivative dyes, and photochromic dyes.

An alternative specific example of a chemical or biological sensing molecule is a crown ether configured for detection of metal ions. In such an embodiment, for example, an 18-crown-6 molecule can be attached to a silicon nanowire. Upon placing the crown ether-attached nanowire in an environment that may include metal ions, if metal ions are present, the metal ions can complex or chelate with the crown ether, resulting in a fluctuation of the conductance. Because of the nanoscale of the nanowires, the conductance can be extremely sensitive to the change of the nanowire surface properties. Thus, small changes in the composition, i.e. complexing or chelating of the metal ions to the crown ethers, can result in small detectable changes in conductance.

Any bridging group (B) that can act to bridge the semi-conducting nanowire to the chemical or biological sensing molecule (through the spacer group) can be used in accordance with the present invention. The bridging group, prior to attachment to the semi-conducting nanowire, typically includes a reactive moiety that is reactive with the semi-conducting nanowire. Exemplary reactive moieties of the bridging group include those having the formula $SiR_3$, where each R can independently be halo, lower alkoxy, or a lower alkyl group (such as methyl, ethyl, propyl, or iso-propyl), with the proviso that at least one R must be reactive with the semi-conducting nanowire, e.g., halo or lower alkoxy. Halo and lower alkoxy are exemplary groups that are reactive for attachment to a silicon surface. Other reactive mechanisms can also be used, such as triflates, acyl, oximes, or amines, for example.

The bridging group (B) can be attached to a spacer group (A) that can be used to tether the chemical or biological sensing molecule to the reactive group (and ultimately, to the semi-conducting nanowire surface). The spacer group, which includes a hydrophilic reactive group that more polar than a carbon-containing moiety to which it is attached, acts to separate the chemical or biological sensing molecule (M) from the surface of the nanowire to maximize the interaction between the chemical or biological sensing molecule (M) and desired chemical or biological substance being tested or analyzed. The spacer group can include various combinations of alkyl, aryl, alkaryl, and aralkyl moieties, and also can include one or more hydrophilic moiety, i.e., more hydrophilic than the alkyl, aryl, alkaryl, or aralkyl moiety to which it is attached. Examples of hydrophilic reactive groups include O, S, amine nitrogen, amide, alkylamide, sulfonyl, sulfonamide, or carbonyl functionalities, for example. The alkyl, aryl and aralkyl moieties can also be substituted by —OH, —SH, —Cl, or the like. Preferably the spacer group can include from about 3 to 10 carbon atoms. Exemplary appropriate spacer groups can include:

—$(CH_2)_b$NH(C)O—, —$(CH_2)_b$O$(CH_2)_a$—, or —$(CH_2)_b$NH—, where a is from 0 to 3 carbons, and b is from 1 to 10 carbons. A specific example of a spacer group as it relates to a bridging group (B) and a chemical or biological sensing molecule (M) is exemplified in Formula 2 below:

$$SiR_3\text{—}(CH_2)_b O(CH_2)_a\text{-M} \qquad \text{Formula 2}$$

In the above example, each R can independently be halo, lower alkoxy, or a lower alkyl group (such as methyl, ethyl, propyl, or iso-propyl), with the proviso that at least one R must be reactive with the semi-conducting nanowire, e.g., halo or lower alkoxy. Other reactive groups that might be used include triflates, acyl, oximes, or amines. In two specific examples, a halo silane reactive group and/or a lower alkyl silane reactive group can be present, as represented by —$SiR_3$. The semi-conducting nanowire is not shown in Formula 2, but can be reactive with one or more of the R groups, and at that point, the —$SiR_3$ portion of Formula 2 will become the bridging group.

In Formula 2, a spacer group is also shown having the formula —$(CH_2)_b O(CH_2)_a$—, wherein a can be from 0 to 3, and b can be from 1 to 10. The spacer group is shown attached to the chemical or biological sensing molecule. Though attached as shown, the chemical or biological sensing molecule should still maintain its functionality for interacting with potential environmental compositions desired to assay. Further, any means or point of attachment (through a spacer group or without a spacer group) between the chemical or biological sensing molecule and the reactive group can be used, provided at least a portion of the functionality of the chemical or biological sensing molecule can be maintained. Further, though a specific type of spacer group is shown, other spacer groups can be used, as would be known by one skilled in the art after reading the present disclosure.

This being stated, a general preparative scheme that can be practiced in accordance with embodiments of the present invention is shown in Formula 3 below:

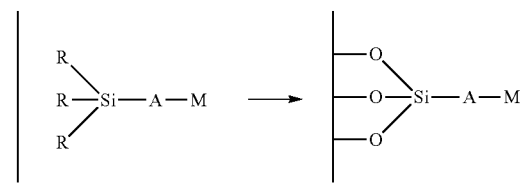

Formula 3

In Formula 3 above, the vertical line represents a semi-conducting nanowire and each R can independently be halo, lower alkoxy, or lower alkyl, e.g., methyl, ethyl, propyl, isopropyl, etc., with the proviso that at least one R must be reactive with the semi-conducting nanowire, e.g., halo or lower alkoxy. Again, reactive groups other than halo or alkoxy can also be used. The example shown in Formula 3 is a lower alkoxy example. Further, in Formula 3, A is a spacer group and M is a chemical or biological sensing molecule.

Though the chemical or biological sensing molecule in Formula 3 above is shown attached to a reagent that is reactive with semi-conducting nanowires, semi-conducting nanowires can alternatively be modified with a reagent that includes a bridging group and a spacer group that is reactive with the chemical or biological sensing molecule. Such a preparative scheme is provided in Formula 4 below:

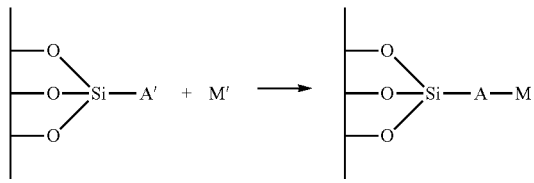

Formula 4

In Formula 4 above, the vertical line represents a semi-conducting nanowire, A' represents a spacer group precursor that includes a moiety that is reactive with a chemical or biological sensing molecule, M' represents a chemical or biological sensing molecule precursor that has a reactive moiety that is reactive with the reactive spacer group precursor, and A-M represents the spacer group covalently attached to the chemical or biological sensing molecule. In one embodiment, the reactive moiety of A' can be a leaving group or a nucleophile, and/or likewise, the reactive moiety of M' can be either a leaving group or nucleophile, provided A' is reactive with M' to form the –A-M portion of the composition.

More specific examples of surface modification are provided in Formulas 5 and 6 below. In Formula 5, an exemplary embodiment is provided wherein a potential sensing molecular unit is immobilized to a reactive reagent, and the reagent is then attached to the semi-conducting nanowires, as shown:

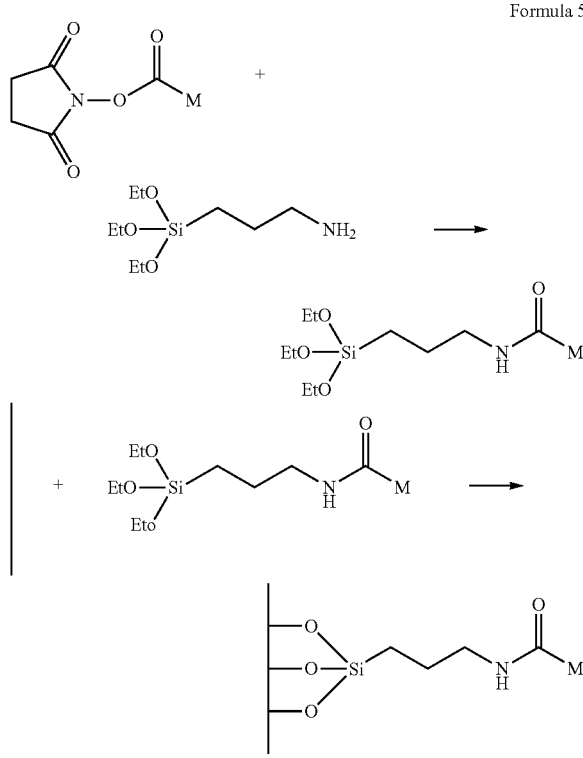

Formula 5

In Formula 5 above, note that the byproducts of the reaction are not shown (and thus, the respective equations are not shown as balanced). Further, in Formula 5, M is a chemical or biological sensing molecule and the vertical line is a semi-conducting nanowire. The chemical or biological sensing molecule can be any of a number of chemical or biological sensing molecular units used as ion indicators, pH indicators, DNA stains, protein stains, enzyme indicators, etc. As shown, the chemical or biological sensing molecule can be treated with commercially available 3-(triethoxysilyl)propylamine, the reaction between the amino group with an activated ester group on the potential sensing molecular unit can occur to form a chemical or biological sensing molecule reagent. The reagent can be reacted with the semi-conducting nanowire to form the chemical or biological sensing molecule-modified semi-conducting nanowire. In other words, when an untreated semi-conducting nanowire is treated with modified potential sensing molecular reagent, a chemical reaction between the triethoxysilyl group and the hydroxy group on the silicon surface can occur, forming a chemical bond, thus immobilizing the potential sensing molecular unit to the silicon substrate.

In Formula 6 below, an alternative method of modifying a semi-conducting nanowire in accordance with embodiments of the present invention is depicted. Specifically, a tri(ethoxy) silylpropylamine, which includes a silane group that is reactive with the semi-conducting nanowires, and further includes a reactive amino group is shown. Specifically, the reactive amino group is reactive with an active ester that is attached to a chemical or biological sensing molecule, as shown:

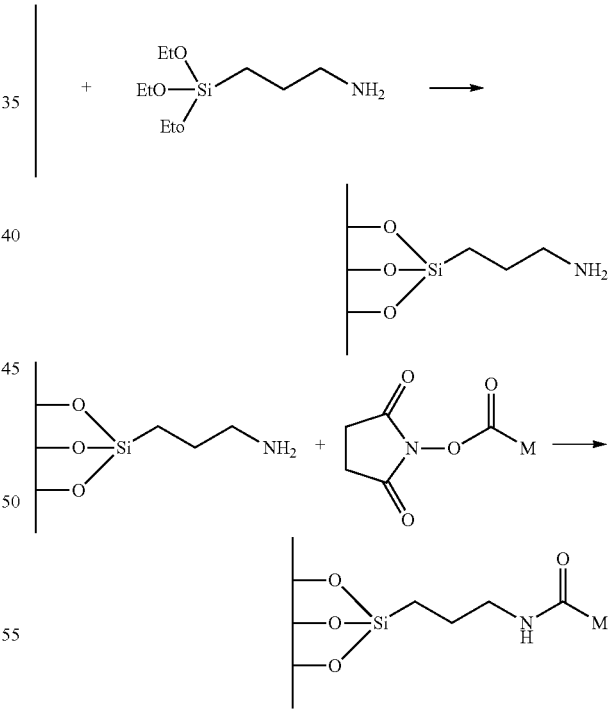

Formula 6

In Formula 6 above, note that the byproducts of the reactions are not shown (and thus, the respective equations are not shown as balanced). Further, in Formula 6, M is a chemical or biological sensing molecule and the vertical line is a semi-conducting nanowire. M can be any of a number of chemical or biological sensing molecular units used as ion indicators, pH indicators, DNA stains, protein stains, enzyme indicators, etc.

It is noteworthy to point out that the specific examples described in Formulas 5-6 above use N-hydroxy succinimide activated ester as an intermediate in connecting desired chemical or biological sensing molecules to the semi-conducting nanowire. However, other types of activated esters, such as 4-nitrophenol ester or mixed anhydrides can also be used for the same purpose, even though they are not explicitly shown in a formula herein.

To provide one example of an embodiment of the present invention, one can consider photochromism. Photochromism can be defined as a reversible phototransformation of a chemical species between two forms. Each form can have different absorption spectra; different physicochemical properties such as refractive index, dielectric constant, and/or oxidation/reduction potential; and different geometrical structure. These molecular property changes can be applied to various photonic devices, which can be used to determine the presence of an analyte in an environment. The immobilization of chemical or biological sensing molecules on nanowires can enable such sensitivities.

Nanowires can be grown using conventional growth techniques, or can be fabricated using fabrication techniques. If grown, one of several methods can be used including chemical vapor deposition (CVD), nanoimprinting, nanotemplating, and/or electrodeposition, to name a few. Alternatively, other schemes for nanowire growth can be carried out as well. For example, nanowire growth material can be provided by ablating a solid target, such as with a laser. Such a method can be carried out with or without a substrate. In other embodiments, fabrication techniques can be carried out, such as high pressure injection methods, e-beam lithographic methods, and nanoimprinting methods.

It is to be understood that the above-referenced arrangements are only illustrative of the application for the principles of the present invention. Numerous modifications and alternative arrangements can be devised without departing from the spirit and scope of the present invention.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Immobilization of a Fluorescent Calcium Ion Indicator onto Silicon Nanowires

Semi-conducting nanowires (1) are treated with 3-(triethoxysilyl)propylamine (2) to form surface modified nanowires (3). Reactive Sc ester functionalized fluorescent calcium ion indicator compositions (4) which are reactive with the amine group of the 3-(triethoxysilyl)propylamine are then used to treat the modified nanowires such that a covalent bond forms between the modified nanowires and the ion indicators. This causes the ion indicators to become tethered to the semi-conducting nanowires such that the receptor unit faces generally away from the semi-conducting nanowires, thus forming fluorescent calcium ion indicator-attached semi-conducting nanowires (5). The preparative scheme is shown generally below:

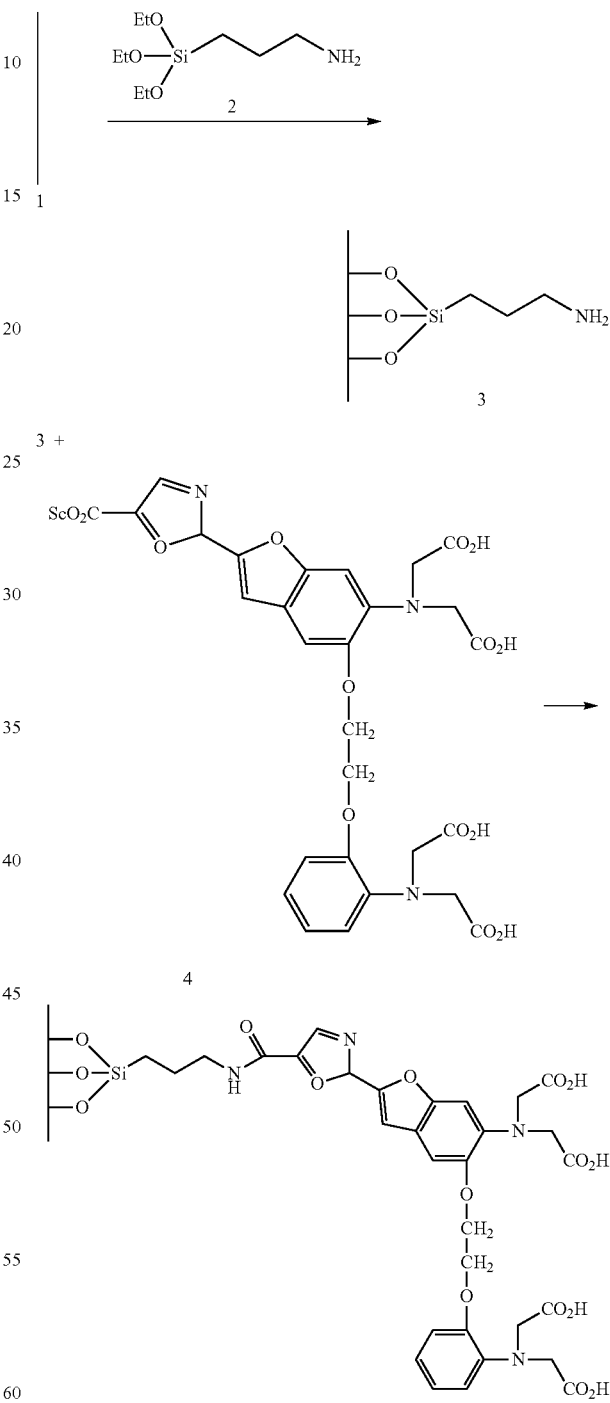

It is to be noted that the byproducts of the reactions are not shown, and thus, the respective equations are not shown as balanced.

Example 2

Immobilization of a Photo Chromic Compound onto Silicon Nanowires

Semi-conducting nanowires (1) are treated with 3-(triethoxysilyl)propylamine (2) to form surface modified nanowires (3). Spiropyran target compositions modified with reactive succinimidyl group (6) that are reactive with the 3-(triethoxysilyl)propylamine are then used to treat the modified nanowires, forming a covalent bond between modified nanowires and the modified spiropyran target composition. The resulting compositions formed are spiropyran target-attached semi-conducting nanowires (7a). Upon exposure to UV light, the compound undergoes an isomerization wherein the spiro linkage is severed, resulting in a highly polar "open" form (7b). Irradiation of the open form at wavelengths near about 530 nm causes the composition to revert to its closed form (7a). Thus, the immobilized spiropyran compound can be switched from a closed to open form with UV light, and from an open to closed form with visible light. The reaction scheme of this preparation is shown below:

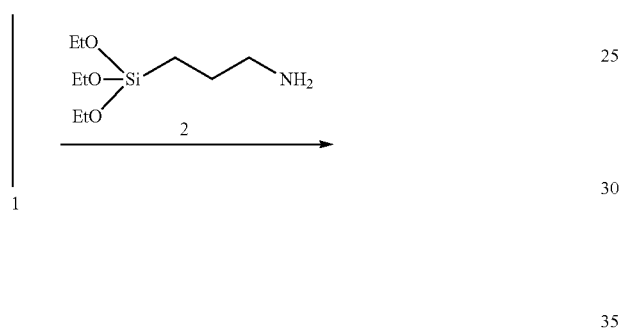

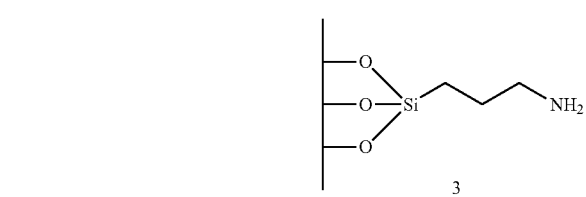

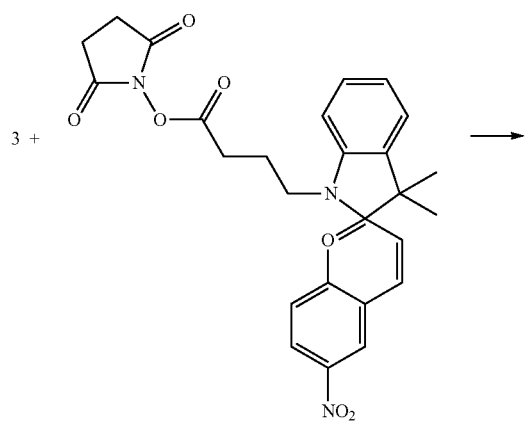

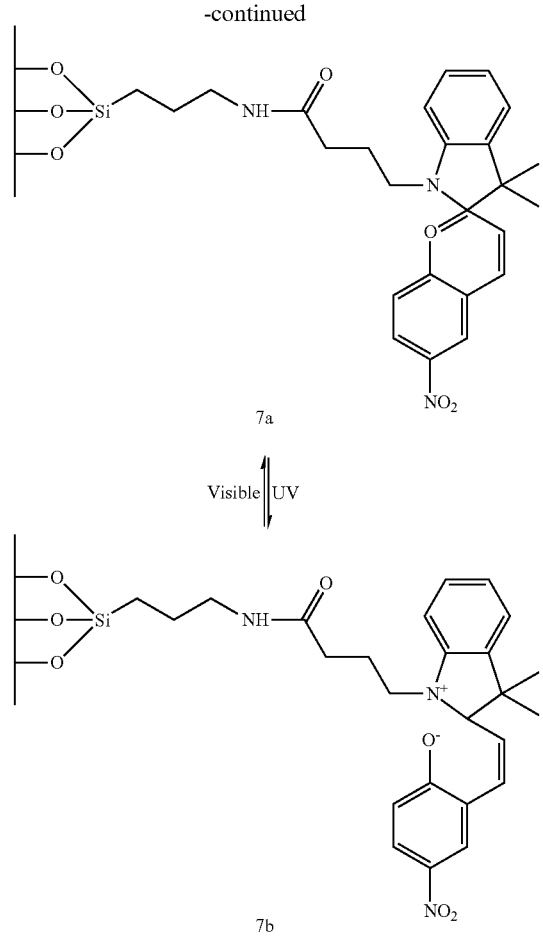

It is to be noted that the byproducts of the reactions are not shown, and thus, the respective equations are not shown as balanced.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A chemical or biological sensor, comprising:
   a) a semi-conducting nanowire; and
   b) a chemical or biological sensing molecule tethered to the semi-conducting nanowire through a spacer group including a hydrophilic reactive group,
   wherein the chemical or biological sensor is configured as formula NW-B-A-M, where NW is the semi-conducting nanowire, B is a bridging group, A is the spacer group including the hydrophilic reactive group, and M is the chemical or biological sensing molecule.

2. A chemical or biological sensor as in claim 1, wherein the semi-conducting nanowire is connected to at least two leads that provide an electrical voltage or current to the semi-conducting nanowire.

3. A chemical or biological sensor as in claim 1, further comprising a signal measurement apparatus electrically connected to the nanowire, said signal measurement apparatus capable of detecting current changes in the Pico ampere range.

4. A chemical or biological sensor as in claim 1, wherein the semi-conducting nanowire has been grown from a substrate.

5. A chemical or biological sensor as in claim 1, wherein the semi-conducting nanowire has been fabricated using a fabrication device.

6. A chemical or biological sensor as in claim 1, wherein the chemical or biological sensing molecule is interactive with a predetermined analyte.

7. A chemical or biological sensor as in claim 6, wherein the chemical or biological sensing molecule is chemically reactive with a predetermined analyte.

8. A chemical or biological sensor as in claim 1, wherein the chemical or biological sensing molecule is configured to sense a predetermined chemical or class of chemicals.

9. A chemical or biological sensor as in claim 1, wherein the chemical or biological sensing molecule is configured to sense a predetermined biological substance or class of biological substances.

10. A chemical or biological sensor as in claim 1, wherein the semi-conducting nanowire has a length to width aspect ratio of at least 5.

11. A chemical or biological sensor as in claim 1, said chemical or biological sensor being configured to detect analytes in a fluid.

12. A chemical or biological sensor as in claim 11, wherein the fluid is a liquid environment.

13. A chemical or biological sensor as in claim 11, wherein the fluid is a gas environment.

14. A chemical or biological sensor as in claim 1, said chemical or biological sensor configured to detect analytes in a solid state.

15. A chemical or biological sensor as in claim 1, wherein said sensor includes an array of semi-conducting nanowires, each of said semi-conducting nanowires having chemical or biological sensing molecules tethered thereto.

16. A chemical or biological sensor as in claim 1, wherein the semi-conducting nanowire is of a material selected from the group consisting of silicon, germanium, gallium arsenide, tin oxide, cadmium sulfide, cadmium telluride, cadmium selenide, and combinations thereof.

17. A chemical or biological sensor as in claim 1, wherein the hydrophilic reactive group is selected from the group consisting of O, S, amine nitrogen, amide, alkylamide, sulfonyl, sulfonamide, and carbonyl.

18. A chemical or biological sensor as in claim 17, wherein the hydrophilic reactive group is an amine.

19. A chemical or biological sensor, comprising:
an array of semi-conducting nanowires, wherein individual semi-conducting nanowires of the array include a chemical or biological sensing molecules tethered thereto through a spacer group including a hydrophilic reactive group; wherein the chemical or biological sensor is configured as formula NW-B-A-M, where NW is the semi-conducting nanowire, B is a bridging group, A is the spacer grotto including the hydrophilic reactive group, and M is the chemical or biological sensing molecule
electrical leads that provide an electrical property to the array; and
a signal measurement apparatus electrically coupled to the array and configured for detecting changes in the electrical property.

20. A chemical or biological sensor as in claim 19, wherein the individual semi-conducting nanowires have been grown from a substrate.

21. A chemical or biological sensor as in claim 19, wherein the individual semi-conducting nanowires have been fabricated using a fabrication device.

22. A chemical or biological sensor as in claim 19, wherein the chemical or biological sensing molecule is interactive with a predetermined analyte.

23. A chemical or biological sensor as in claim 22, wherein the chemical or biological sensing molecule is chemically reactive with a predetermined analyte.

24. A chemical or biological sensor as in claim 19, wherein the chemical or biological sensing Molecule is configured to sense a predetermined chemical or class of chemicals.

25. A chemical or biological sensor as in claim 19, wherein the chemical or biological sensing molecule is configured to sense a predetermined biological substance or class of biological substances.

26. A chemical or biological sensor as in claim 19, wherein the individual semi-conducting nanowires have a length to width aspect ratio or at least 5.

27. A chemical or biological sensor as in claim 19, said chemical or biological sensor being configured to detect analytes in a fluid.

28. A chemical or biological sensor as in claim 27, wherein the fluid is a liquid environment.

29. A chemical or biological sensor as in claim 27, wherein the fluid is, a gas environment.

30. A chemical or biological sensor as in claim 19, said chemical or biological sensor configured to detect analytes in a solid state.

31. A chemical or biological sensor as in claim 19, wherein the semi-conducting nanowire is of a material selected from the group consisting of silicon, germanium, gallium arsenide, tin oxide, cadmium sulfide, cadmium telluride, cadmium selenide, and combinations thereof.

32. A chemical or biological sensor as in claim 19, wherein the electrical property is electrical current carried by the individual semi-conducting nanowires of the array.

33. A chemical or biological sensor as in claim 19, wherein the hydrophilic reactive group is selected from the group consisting of O, S, amine nitrogen, amide, alkylamide, sulfonyl, sulfonamide, and carbonyl.

34. A chemical or biological sensor as in claim 33, wherein the hydrophilic reactive group is an amine.

35. A chemical or biological sensor as in claim 19, wherein the array of semi-conducting nanowires includes freestanding nanowires.

36. A method of detecting the presence of an analyte in an environment, comprising:
a) generating a current along a nanowire sensing element of a chemical or biological sensor, said nanowire sensing element including:
i) a semi-conducting nanowire; and
ii) a chemical or biological sensing molecule tethered to the semi-conducting nanowire through a spacer group including a hydrophilic reactive group; wherein the chemical or biological sensor is configured as formula NW-B-A-M, where NW is the semi-conducting nanowire, B is a bridging group, A is the spacer group including the hydrophilic reactive group, and M is the chemical or biological sensing molecule
b) exposing the nanowire sensing element carrying the current to an environment suspected of containing an analyte that is interactive with the chemical or biological sensing molecule; and
c) determining whether the current is altered as a result of the analyte interacting with the chemical or biological sensing molecule.

37. A method as in claim 36, wherein the semi-conducting nanowire has been grown from a substrate.

38. A method as in claim 36, wherein semi-conducting nanowire has been fabricated using fabrication tools.

39. A method as in claim 36, wherein the chemical or biological sensing molecule is interactive with a predetermined analyte.

40. A method as in claim 39, wherein the chemical or biological sensing molecule is chemically reactive with a predetermined analyte.

41. A method as in claim 36, wherein the chemical or biological sensing molecule is configured to sense a predetermined chemical or class of chemicals.

42. A method as in claim 36, wherein the chemical or biological sensing molecule is configured to sense a predetermined biological substance or class of biological substances.

43. A method as in claim 36, wherein the semi-conducting nanowire has a length to Width aspect ratio of at least 5.

44. A method as in claim 36, said chemical or biological sensor configured to detect analytes in a fluid.

45. A method as in claim 44, wherein the fluid is a liquid environment.

46. A method as in claim 44, wherein the fluid is a gas environment.

47. A method as in claim 36, said chemical or biological sensor configured to detect analytes in a solid state.

48. A method as in claim 36, wherein the semi-conducting nanowire is of a material selected from the group consisting of silicon, germanium, gallium arsenide, tin oxide, cadmium sulfide, cadmium telluride, cadmium selenide, and combinations thereof.

49. A method as in claim 36, wherein the hydrophilic reactive group is selected from the group consisting of O, S, amino nitrogen, amide, alkylamide, sulfonyl, sulfonamide, and carbonyl.

50. A method as in claim 49, wherein the hydrophilic reactive group is an amine.

51. A chemical or biological sensor as in claim 1, wherein the sensing molecule is a fluorescent dye.

52. A chemical or biological sensor as in claim 1, wherein the sensing molecule is a crown ether configured for detection of metal ions.

53. A chemical or biological sensor as in claim 19, wherein the sensing molecule is a fluorescent dye.

54. A chemical or biological sensor as in claim 19, wherein the sensing molecule is a crown ether configured for detection of metal ions.

55. A method as in claim 36, wherein the sensing molecule is a fluorescent dye.

56. A method as in claim 36, wherein the sensing molecule is a crown ether configured for detection of metal ions.

* * * * *

UNITED STATES PATENT AND TRADEMARK OFFICE
CERTIFICATE OF CORRECTION

PATENT NO.         : 8,048,377 B1
APPLICATION NO.    : 10/795730
DATED              : November 1, 2011
INVENTOR(S)        : Zhang-Lin Zhou et al.

It is certified that error appears in the above-identified patent and that said Letters Patent is hereby corrected as shown below:

In column 13, line 57, in Claim 19, delete "grotto" and insert -- group --, therefor.

In column 14, line 11, in Claim 24, delete "Molecule" and insert -- molecule --, therefor.

In column 14, line 19, in Claim 26, delete "or" and insert -- of --, therefor.

In column 14, line 26, in Claim 29, delete "is," and insert -- is --, therefor.

In column 15, line 19, in Claim 43, delete "Width" and insert -- width --, therefor.

In column 16, line 8, in Claim 49, delete "amino" and insert -- amine --, therefor.

Signed and Sealed this
Seventeenth Day of July, 2012

David J. Kappos
*Director of the United States Patent and Trademark Office*